United States Patent
Tanaka

(10) Patent No.: US 10,444,377 B2
(45) Date of Patent: Oct. 15, 2019

(54) RADIATION IMAGING SYSTEM, RADIATION IMAGING APPARATUS, RADIATION IMAGING METHOD, AND COMPUTER-READABLE MEDIUM

(71) Applicant: CANON KABUSHIKI KAISHA, Tokyo (JP)

(72) Inventor: Ryo Tanaka, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 15/906,463

(22) Filed: Feb. 27, 2018

(65) Prior Publication Data

US 2018/0246225 A1    Aug. 30, 2018

(30) Foreign Application Priority Data

Feb. 28, 2017 (JP) .................. 2017-035851

(51) Int. Cl.
  *A61B 6/00* (2006.01)
  *G01T 1/17* (2006.01)
  *G01T 1/161* (2006.01)

(52) U.S. Cl.
  CPC ............ *G01T 1/17* (2013.01); *A61B 6/548* (2013.01); *A61B 6/566* (2013.01); *G01T 1/161* (2013.01); *A61B 6/563* (2013.01)

(58) Field of Classification Search
  None
  See application file for complete search history.

(56) References Cited

U.S. PATENT DOCUMENTS

| 2014/0254758 A1* | 9/2014 | Saigusa | A61B 6/545 378/62 |
| 2014/0294278 A1* | 10/2014 | Semba | G06F 19/321 382/132 |
| 2016/0166227 A1* | 6/2016 | Tanaka | A61B 6/563 382/132 |
| 2017/0360390 A1* | 12/2017 | Tajima | A61B 6/12 |

FOREIGN PATENT DOCUMENTS

JP    2004-147921 A    5/2004

* cited by examiner

*Primary Examiner* — Edwin C Gunberg
(74) *Attorney, Agent, or Firm* — Carter, DeLuca & Farrell LLP

(57) ABSTRACT

Provided is a radiation imaging system including: a first radiation imaging apparatus, which is configured to be capable of taking a first radiation image based on first examination information; a second radiation imaging apparatus, which is configured to be capable of taking a second radiation image based on second examination information; and a control unit, which is configured to control imaging of the second radiation image in the second radiation imaging apparatus based on progress information related to imaging of the first radiation image in the first radiation imaging apparatus when predetermined examination information is duplicated between the first examination information and the second examination information.

25 Claims, 8 Drawing Sheets

FIG. 2

| EXAMINATION ID | PATIENT ID | PATIENT NAME | SEX | DATE OF BIRTH | ADDRESS |
|---|---|---|---|---|---|
| 001 | P111 | EEE EEE | M | 1981/11/11 | 201 |
| 002 | P777 | AAA AAA | M | 2002/02/02 | 301 |
| 003 | P333 | CCC CCC | F | 1977/07/07 | 402 |
| 004 | P444 | BBB BBB | M | 1955/05/05 | 202 |
| 005 | P888 | DDD DDD | F | 1976/06/06 | 401 |
| 006 | P222 | FFF FFF | F | 1964/04/04 | 403 |
| 007 | P555 | GGG GGG | M | 2003/03/03 | 302 |

PATIENT NAME:
DATE OF BIRTH:
PATIENT ID:
AGE:
SEX: ○ MALE ○ FEMALE

PATIENT NAME: BBB BBB
PATIENT ID: P444
DATE OF BIRTH: 1955/06/06
SEX: M

EXAMINATION ID: 0004
FRONT OF BREAST
SIDE OF BREAST

START EXAMINATION 201, 202, 203, 204, 205

FIG. 4A

| EXAMINATION ID | STATUS |
|---|---|
| 001 | AVAILABLE TO START |
| 002 | AVAILABLE TO START |
| 003 | AVAILABLE TO START |

FIG. 4B

| EXAMINATION ID | STATUS |
|---|---|
| 001 | AVAILABLE TO START |
| 002 | AVAILABLE TO START |
| 003 | UNAVAILABLE TO START |

FIG. 4C

| EXAMINATION ID | STATUS |
|---|---|
| 001 | AVAILABLE TO START |
| 002 | AVAILABLE TO START |

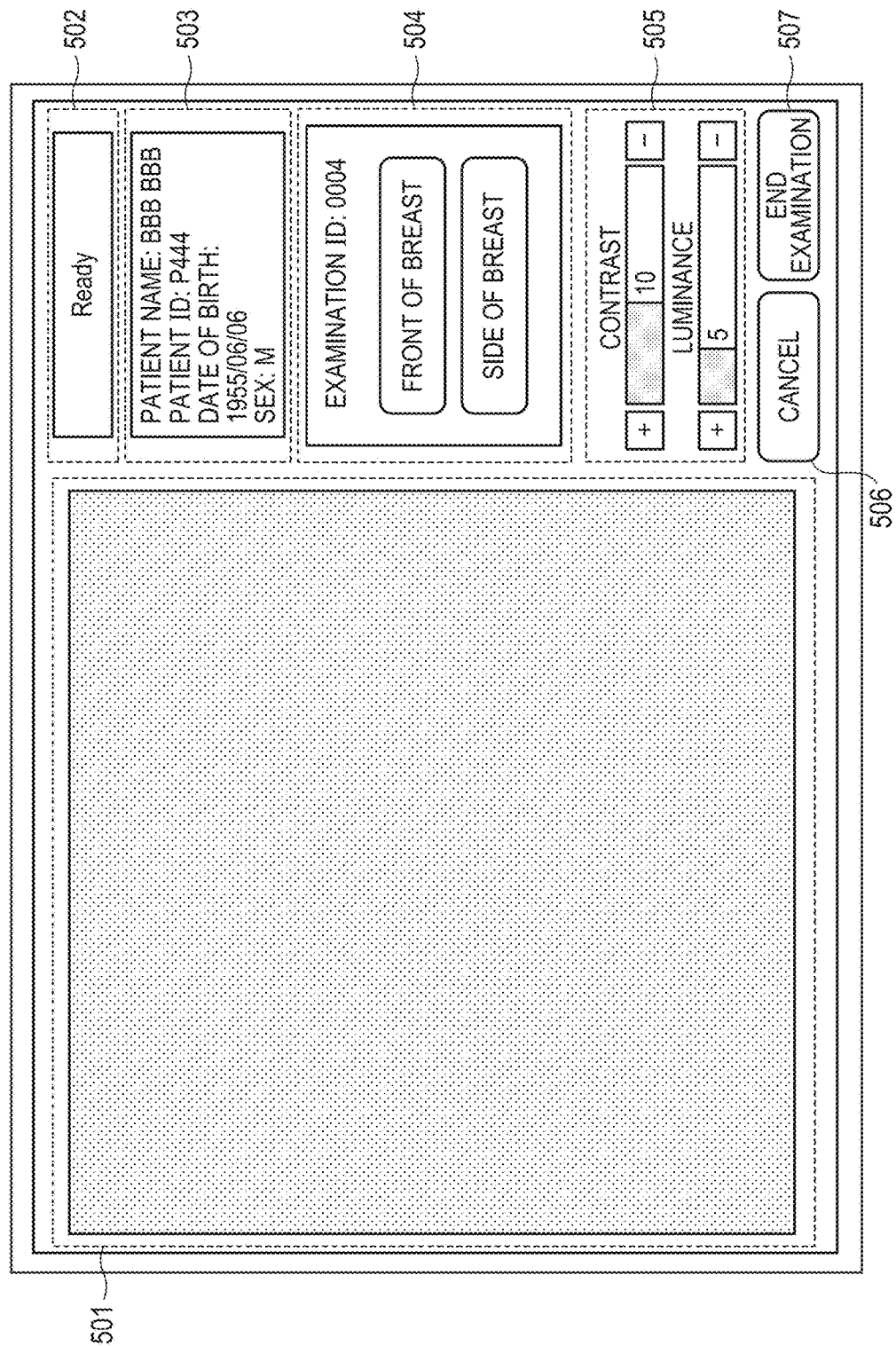

FIG. 8A

| EXAMINATION ID | STATUS |
|---|---|
| 001 | UNPERFORMED |
| 002 | UNPERFORMED |
| 003 | UNPERFORMED |

FIG. 8B

| EXAMINATION ID | STATUS |
|---|---|
| 001 | UNPERFORMED |
| 002 | UNPERFORMED |
| 003 | EXAMINATION STARTED |

FIG. 8C

| EXAMINATION ID | STATUS |
|---|---|
| 001 | UNPERFORMED |
| 002 | UNPERFORMED |
| 003 | EXAMINATION ENDED |

RADIATION IMAGING SYSTEM, RADIATION IMAGING APPARATUS, RADIATION IMAGING METHOD, AND COMPUTER-READABLE MEDIUM

BACKGROUND OF THE INVENTION

Field of the Invention

The present invention relates to a radiation imaging system, a radiation imaging apparatus, a radiation imaging method, and a computer-readable medium.

Description of the Related Art

In recent years, hospital information systems have been constructed in hospitals through network connection. For example, when it is determined that radiation imaging is required, an examination instruction is input through a terminal of a hospital information system (HIS) so as to be transmitted to a radiology department requested to perform the radiation imaging.

This request information is referred to as "examination order". The examination order includes a name of a department that has requested the radiation imaging, an examination item, and personal data of a patient. When the radiology department receives the examination order by a radiology information system (RIS), the radiology department adds imaging conditions and the like to the examination order, and transmits the resultant examination order to a radiation imaging apparatus as examination information. The radiation imaging apparatus performs radiation imaging in accordance with the received examination order. The taken image is added to the examination information, and the resultant examination information is transmitted to a picture archiving and communication system (PACS) or printed to be output.

A method disclosed in Japanese Patent Application Laid-Open No. 2004-147921 involves transmitting examination progress information to an information management apparatus present on a network to manage completion of the examination. In the method of Japanese Patent Application Laid-Open No. 2004-147921, however, when a plurality of radiation imaging apparatus are present on the network, it is difficult for the radiation imaging apparatus to mutually grasp the acquired examination order or a progress thereof.

In the related-art hospital information system in which a plurality of radiation imaging apparatus are connected by a network, it has been difficult for the radiation imaging apparatus to grasp the examination progresses of other radiation imaging apparatus. Therefore, an operator (e.g., a technician or a doctor) who has seen the same examination order on a plurality of radiation imaging apparatus may start the same examination in each of the radiation imaging apparatus, and thus the operation has been inefficient. Further, there has been a problem in that, when the examination is performed without the operator noticing the duplication of the same examination order in the plurality of radiation imaging apparatus, the patient is unnecessarily exposed to radiation.

SUMMARY OF THE INVENTION

According to one embodiment of the present invention, there is provided a radiation imaging system including: a first radiation imaging apparatus, which is configured to be capable of taking a first radiation image based on first examination information; a second radiation imaging apparatus, which is configured to be capable of taking a second radiation image based on second examination information; and a control unit, which is configured to control imaging of the second radiation image in the second radiation imaging apparatus based on progress information related to imaging of the first radiation image in the first radiation imaging apparatus when predetermined examination information is duplicated between the first examination information and the second examination information.

Further features of the present invention will become apparent from the following description of exemplary embodiments with reference to the attached drawings.

BRIEF DESCRIPTION OF THE DRAWINGS

FIG. 2 is a diagram for illustrating an example of an examination information list display screen.

FIG. 4A is a table for showing an example of progress information in the first embodiment.

FIG. 4B is a table for showing an example of progress information in the first embodiment.

FIG. 4C is a table for showing an example of progress information in the first embodiment.

FIG. 5 is a diagram for illustrating an example of an imaging screen obtained before imaging.

FIG. 8A is a table for showing an example of progress information in the second embodiment.

FIG. 8B is table for showing an example of progress information in the second embodiment.

FIG. 8C is a table for showing an example of progress information in the second embodiment.

DESCRIPTION OF THE EMBODIMENTS

Preferred embodiments of the present invention will now be described in detail in accordance with the accompanying drawings. A radiation imaging system according to embodiments of the present invention at least includes a first radiation imaging apparatus configured to be capable of taking a first radiation image based on first examination information and a second radiation imaging apparatus configured to be capable of taking a second radiation image based on second examination information. In the embodiments described below, radiation is not limited to an X-ray, and may be, for example, an electromagnetic wave, an α-ray, a β-ray, or a γ-ray.

First Embodiment

Figure 1:
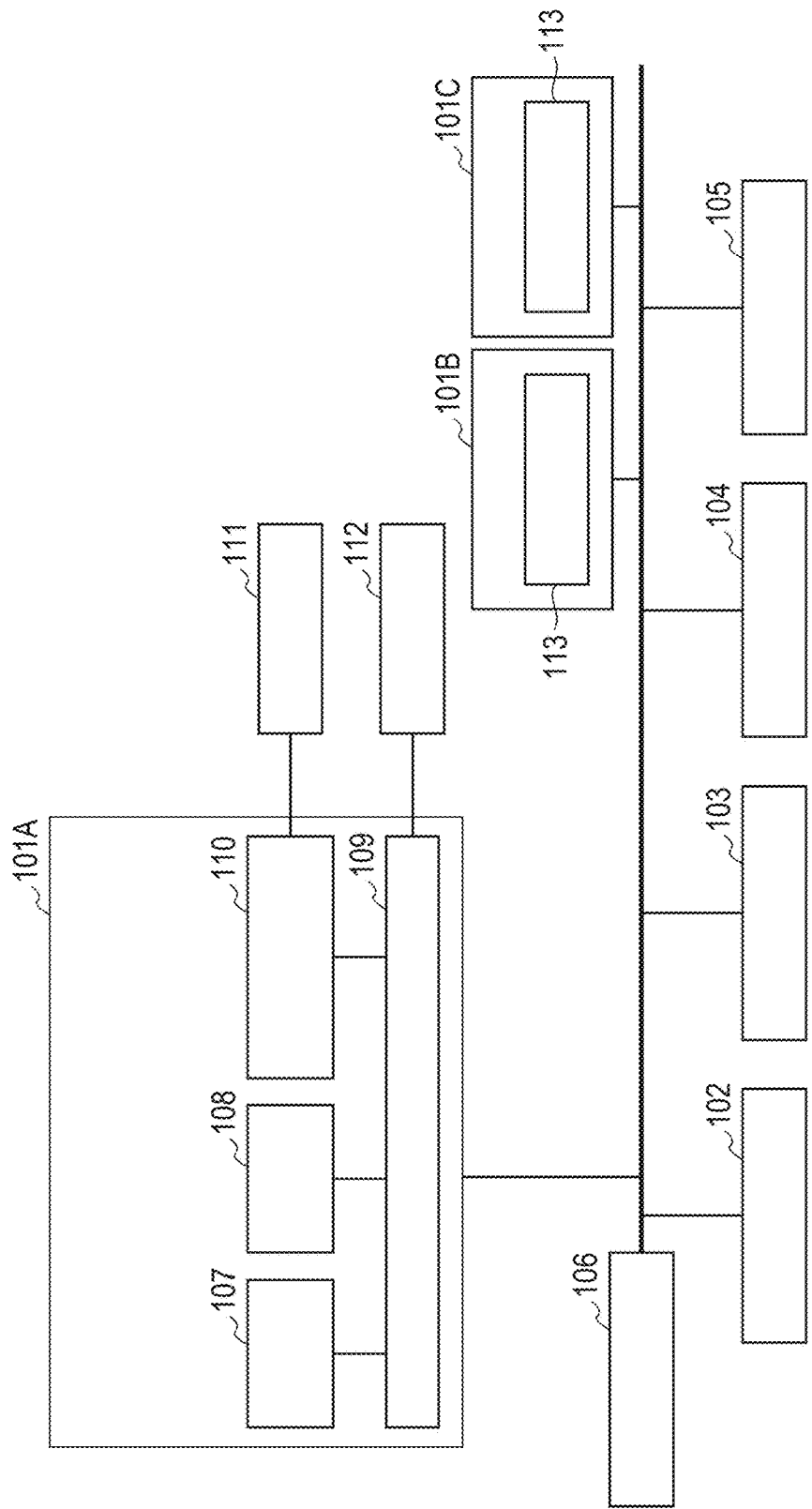
FIG. 1 is a diagram for illustrating an example of a configuration of a radiation imaging system according to a first embodiment of the present invention.

FIG. 1 is a diagram for illustrating an example of a configuration of a radiation imaging system according to a first embodiment of the present invention.

As illustrated in FIG. 1, the radiation imaging system includes radiation imaging apparatus 101A to 101C, an HIS (in-hospital system) 102, a radiology information system (RIS) 103, and a PACS (image server) 104. In FIG. 1, the radiation imaging apparatus 101A corresponds to the first radiation imaging apparatus, and the radiation imaging apparatus 101B and 101C correspond to the second radiation imaging apparatus.

Further, the radiation imaging apparatus 101A to 101C, the HIS 102, the RIS 103, the PACS 104, and a printer 105 are electrically connected to one another via a network 106 constructed by, for example, a local area network (LAN) or a wide area network (WAN).

Each of those radiation imaging apparatus includes one or more computers. For example, the computer includes a main control unit, for example, a CPU, and a storage, for example, a read only memory (ROM) and a random access memory (RAM). The computer may also include a communication unit, for example, a network card, and an input/output unit, a keyboard, a display, or a touch panel. Those units of the computer are connected to one another via a bus, for example, and are controlled by the main control unit executing programs stored in the storage.

The above is the description of the example of the configuration of the radiation imaging system. The configuration illustrated in FIG. 1 is merely an example, and the apparatus to be connected and the number of the apparatus can be changed as appropriate. For example, in FIG. 1, the HIS 102 and the PACS 104 are connected to the radiation imaging apparatus 101 via the network 106, but the radiation imaging apparatus 101 may not be connected to those apparatus.

In this case, each of the radiation imaging apparatus 101A to 101C includes an imaging apparatus display unit 107, an imaging apparatus operation unit 108, an imaging apparatus control unit (control unit) 109, and a radiation generator control unit 110. Each of the radiation imaging apparatus 101B and 101C further includes a determination unit 113. The radiation imaging apparatus 101A may also include the determination unit 113.

The imaging apparatus display unit 107 is implemented by, for example, a liquid crystal display, and displays various types of information to an operator (e.g., an imaging technician or a doctor). The imaging apparatus operation unit 108 is implemented by, for example, a mouse and an operation button, and inputs various types of instructions from the operator to respective components of the apparatus. The imaging apparatus display unit 107 and the imaging apparatus operation unit 108 may be implemented as a touch panel in which those units are integrally formed. The imaging apparatus control unit 109 integrally controls the processing performed in the radiation imaging apparatus 101A to 101C.

The radiation generator control unit 110 is connected to a radiation generator 111 through wired or wireless communication, and controls radiation irradiation from the radiation generator 111. The radiation generator 111 is implemented by, for example, a radiation-emitting tube, and irradiates a subject to be examined (e.g., a specific part of a patient) with radiation. Examples of the radiation generator 111 include an apparatus of a type that is fixed to an imaging room and an apparatus of a type for round visits or disasters that can be moved to any place.

The radiation imaging apparatus 101A is connected to a radiation detector 112 so that wired or wireless communication is enabled therebetween, and electric power, image signals, control signals, and the like are transmitted or received between those apparatus. The radiation detector 112 functions as a detector configured to detect the radiation that has passed through the subject to acquire a radiation image of the subject. That is, the radiation generator 111 and the radiation detector 112 cooperate with each other to achieve radiation imaging.

The radiation imaging apparatus 101A can acquire the first examination information from the RIS 103 via the network 106 to store the acquired first examination information in the storage of the radiation imaging apparatus 101A. Each of the radiation imaging apparatus 101B and 101C can acquire the second examination information from the RIS 103 via the network 106 to store the acquired second examination information in the storage of each of the radiation imaging apparatus 101B and 101C.

Further, the radiation imaging apparatus 101A can store a status of the radiation imaging (first progress information) in association with each stored examination. Each of the radiation imaging apparatus 101B and 101C can store a status of the radiation imaging (second progress information) in association with each stored examination. The status in initial setting of each examination is "examination is available to start" or "unperformed".

The radiation imaging apparatus 101A to 101C of FIG. 1 have the same function as the function described above, and the respective radiation imaging apparatus 101A to 101C can be individually distinguished. In the following, when the radiation imaging apparatus 101A to 101C are not required to be individually distinguished, the apparatus is simply referred to as "radiation imaging apparatus 101".

The RIS 103 performs information management of, for example, examination information and examination progress information. The examination information includes a subject name, a subject ID, a date of birth, sex, an examination ID, an examination date/time, an examination place, and an imaging procedure. The examination progress information includes at least one of examination start, examination end, or examination cancel.

Next, the operation of the radiation imaging system illustrated in FIG. 1 is described. The radiation imaging system of the first embodiment avoids starting the same examination in a duplicated manner along the flow of the examination.

First, the imaging apparatus control unit 109 of the radiation imaging apparatus 101A acquires the first examination information from the RIS 103 configured to manage the examination information, and stores the first examination information.

As illustrated in FIG. 2, the radiation imaging apparatus 101A displays the examination information on an examination information list screen. The examination information list screen includes a search condition input section 201, an examination information selection section 202, a patient information display section 203, an examination information display section 204, and an examination start button 205.

When the search condition input section 201 inputs a search condition, the examination information matching with the search condition among the examination information stored in the radiation imaging apparatus 101 is displayed in the examination information selection section 202. When the examination information is selected in the examination information selection section 202, patient information of the examination concerned is displayed in the patient information display section 203, and an imaging method is displayed in the examination information display section 204.

When the operator selects the first examination information to be performed from the examination information selection section 202 and presses the examination start button 205, the radiation imaging apparatus 101A verifies the status stored in association with the examination.

When the status is "examination is unavailable to start", the radiation imaging apparatus 101A displays an alert to inform the operator by an alert display that the examination has already been started in any one of the radiation imaging apparatus 101B and 101C. Further, when the status is "examination is unavailable to start", the radiation imaging apparatus 101A may avoid starting the examination in a duplicated manner by inhibiting transition from the examination information list screen to an imaging screen. At this time, the radiation imaging apparatus 101A may be informed of an installation place of the radiation imaging apparatus 101 that has started the examination earlier or the name of the operator using the apparatus.

When the status is "examination is available to start", the radiation imaging apparatus 101A informs the radiation imaging apparatus 101B and 101C of the examination start of the examination concerned. The imaging apparatus control unit 109 of the radiation imaging apparatus 101A transmits the first progress information to the radiation imaging apparatus 101B and 101C.

Figure 3:
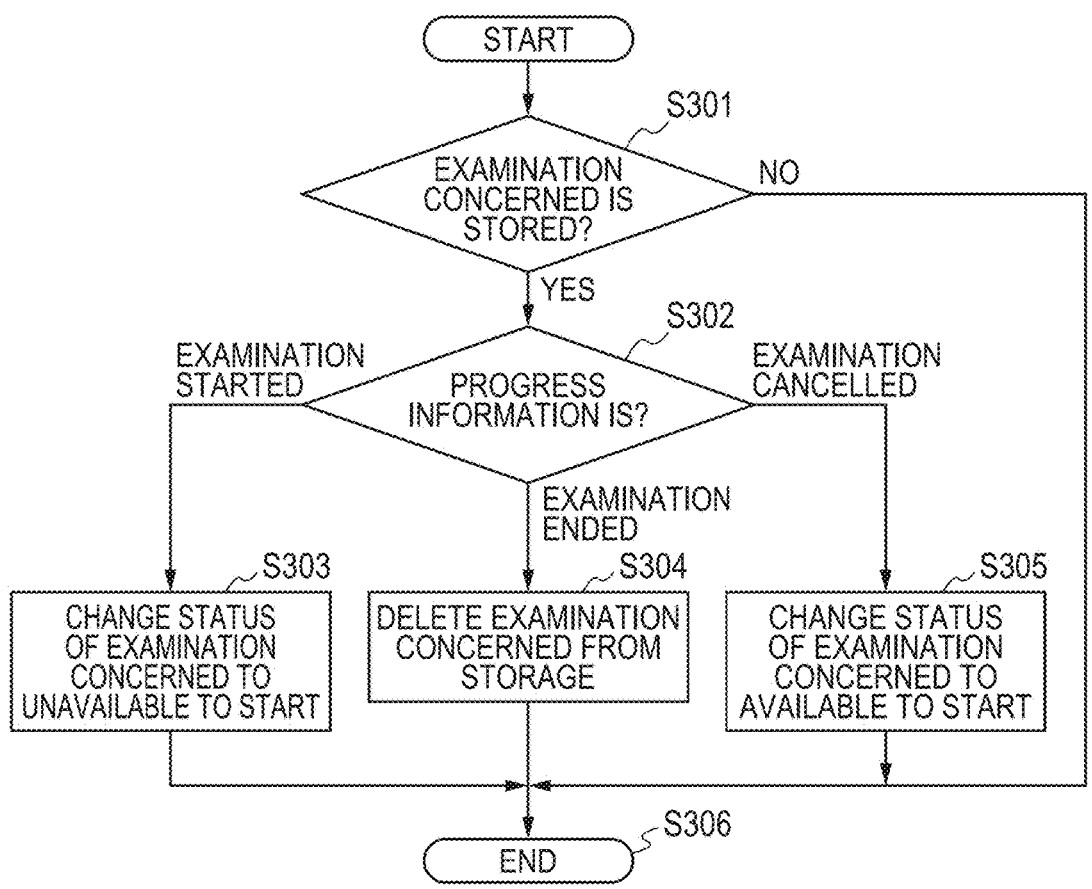
FIG. 3 is a flow chart for illustrating an example of processing performed by a radiation imaging apparatus in the first embodiment.

FIG. 3 is a flow chart for illustrating an example of the processing performed by the radiation imaging apparatus 101. Each of the radiation imaging apparatus 101B and 101C that has been informed of the examination start from the radiation imaging apparatus 101A determines whether or not the second examination information corresponding to the first examination information related to the first progress information is stored in the storage of each of the radiation imaging apparatus 101B and 101C (Step S301).

When the examination information is not stored, the processing is ended (Step S306). When the examination information is stored, each of the radiation imaging apparatus 101B and 101C verifies the details of the acquired progress information (Step S302). The determination unit 113 of each of the radiation imaging apparatus 101B and 101C acquires the first examination information of the radiation imaging apparatus 101A to determine the duplication between the first examination information and the second examination information.

When predetermined examination information is duplicated between the first examination information and the second examination information, the imaging apparatus control unit 109 of each of the radiation imaging apparatus 101B and 101C controls the imaging of the second radiation image based on the first progress information of the imaging of the first radiation image.

When it is verified that the first progress information corresponds to examination start, each of the radiation imaging apparatus 101B and 101C changes the status of the examination concerned to "examination is unavailable to start" as from FIG. 4A to FIG. 4B (Step S303), and stores the change. In this case, the radiation imaging apparatus 101A may also change the status of the examination concerned to "examination is unavailable to start" as from FIG. 4A to FIG. 4B and store the change.

As described above, when the imaging apparatus control unit 109 of each of the radiation imaging apparatus 101B and 101C acquires the first progress information representing that the imaging of the first radiation image is started, the imaging apparatus control unit 109 of each of the radiation imaging apparatus 101B and 101C does not permit the imaging of the second radiation image. When the imaging apparatus control unit 109 of each of the radiation imaging apparatus 101B and 101C acquires the first progress information representing that the imaging of the first radiation image is started, the imaging apparatus control unit 109 of each of the radiation imaging apparatus 101B and 101C updates the second progress information to progress information representing that the imaging of the second radiation image is unavailable to start.

After the radiation imaging apparatus 101A completes the informing of the examination start to the radiation imaging apparatus 101B and 101C, the radiation imaging apparatus 101A informs the RIS 103 of the examination start of the examination concerned. The imaging apparatus control unit 109 of the radiation imaging apparatus 101A transmits the first progress information to the RIS (information management unit) 103.

After the radiation imaging apparatus 101A completes the informing of the examination start to the RIS 103, in the radiation imaging apparatus 101A, the imaging screen of FIG. 5 is displayed on the imaging apparatus display unit 107, and the examination is started.

The imaging screen includes an image display section 501, a radiation detector state display section 502, a patient information display section 503, an imaging method display section 504, an image processing adjustment section 505, a cancel button 506, and an examination end button 507. The cancel button 506 changes to an examination holding button 508 of FIG. 6 at a time point at which one or more radiation images are taken.

The operator sees the patient information display section 503 and the imaging method display section 504 to perform setting of the imaging and positioning of the patient. When the radiation detector 112 enters an imageable state, a "ready message" representing the imageable state is displayed in the radiation detector state display section 502. The operator presses a radiation irradiation switch (not shown) after seeing the "ready message".

Figure 6:
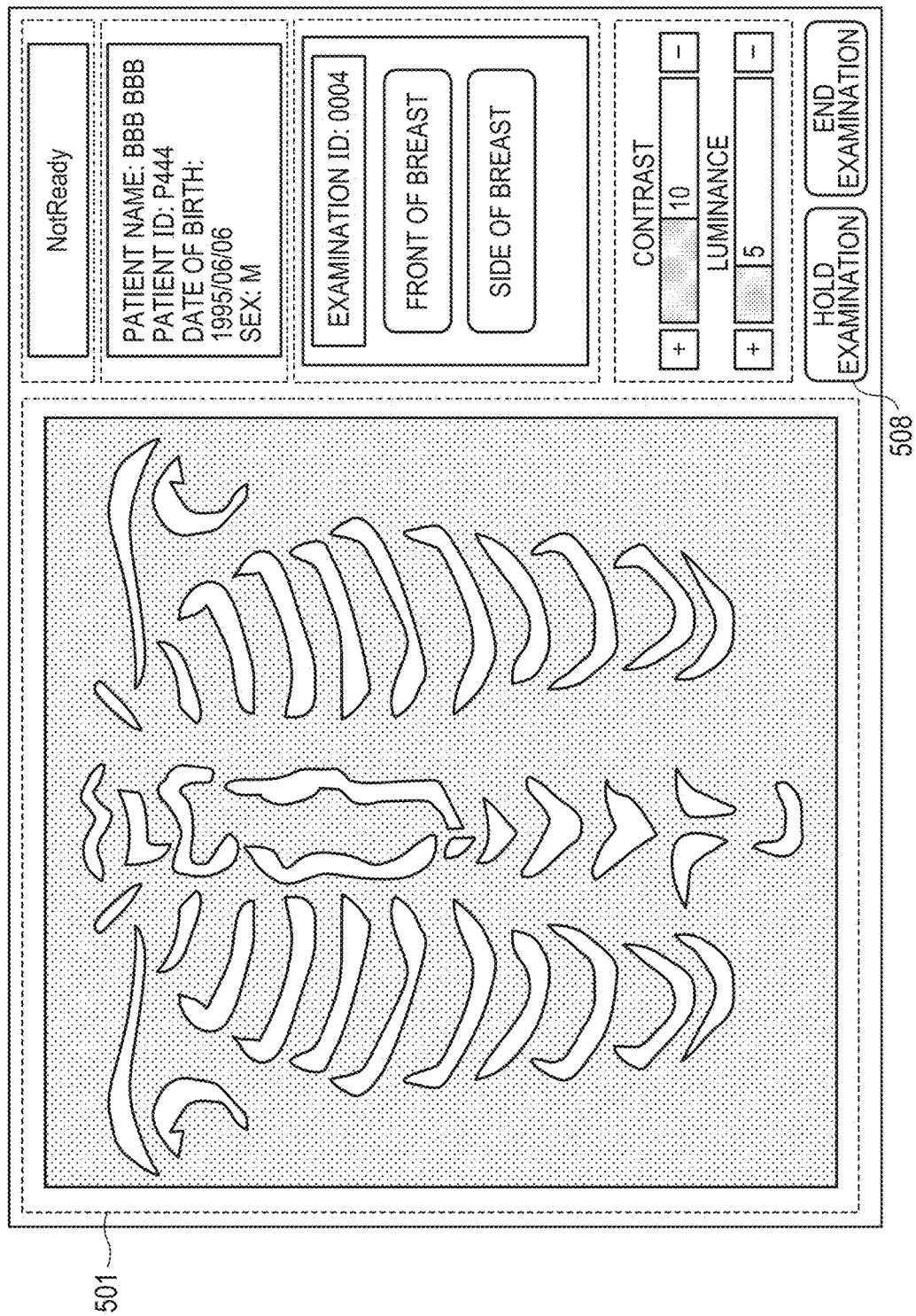
FIG. 6 is a diagram for illustrating an example of the imaging screen obtained after imaging.

At this time, as illustrated in FIG. 6, the radiation detected by the radiation detector 112 is displayed as a radiation image in the image display section 501. The operator can operate the image processing adjustment section 505 to adjust the contrast or the luminance of the displayed radiation image.

After imaging of all of the radiation images is completed, the operator presses the examination end button 507 displayed on the imaging screen. In this manner, the examination is ended, and the taken radiation image is output to the PACS 104, the printer 105, and the storage of the own apparatus. Further, the examination information list screen is displayed on the imaging apparatus display unit 107. At this time, the radiation imaging apparatus 101A informs the RIS 103 of the examination end of the examination concerned. The imaging apparatus control unit 109 of the radiation imaging apparatus 101A transmits the first progress information to the RIS (information management unit) 103.

After the informing of the examination end to the RIS 103 is completed, the radiation imaging apparatus 101A informs the radiation imaging apparatus 101B and 101C of the examination end of the examination concerned. The radiation imaging apparatus 101A may delete the examination information from the storage as from FIG. 4B and FIG. 4C after confirming the examination end.

Next, a case in which the examination is ended in the radiation imaging apparatus 101A as described above is described. Each of the radiation imaging apparatus 101B and 101C that has been informed of the examination end from the radiation imaging apparatus 101A determines whether or not the examination information related to the progress information is stored in the storage (Step S301).

When the examination information is not stored, the processing is ended (Step S306).

When the examination information is stored, each of the radiation imaging apparatus 101B and 101C verifies the details of the acquired progress information (Step S302). When each of the radiation imaging apparatus 101B and 101C confirms the examination end, each of the radiation imaging apparatus 101B and 101C deletes the examination information from the storage as from FIG. 4B and FIG. 4C (Step S304). The examination deleted from the storage is no longer displayed on the examination information list screen.

As described above, when the imaging apparatus control unit 109 of each of the radiation imaging apparatus 101B and 101C acquires the first progress information representing that the imaging of the first radiation image is ended, the imaging apparatus control unit 109 of each of the radiation imaging apparatus 101B and 101C deletes the second examination information from the storage of each of the radiation imaging apparatus 101B and 101C.

Next, description is given of a case in which the radiation imaging apparatus 101A cancels the examination due to the physical condition of the subject or for the sake of operation after the examination is started. In this case, the operator presses the cancel button 506 displayed on the imaging screen in order to cancel the examination. In this manner, the examination is canceled, and the examination information list screen is displayed on the imaging apparatus display unit 107. At this time, the radiation imaging apparatus 101A informs the RIS 103 of the examination cancel of the examination concerned. The imaging apparatus control unit 109 of the radiation imaging apparatus 101A transmits the first progress information to the RIS (information management unit) 103.

After the informing of the examination cancel to the RIS 103 is completed, the radiation imaging apparatus 101A informs the radiation imaging apparatus 101B and 101C of the examination cancel of the examination concerned.

Each of the radiation imaging apparatus 101B and 101C that has been informed of the examination cancel from the radiation imaging apparatus 101A determines whether or not the examination information related to the progress information is stored in the storage (Step S301). When the examination information is not stored, the processing is ended (Step S306). When the examination information is stored, each of the radiation imaging apparatus 101B and 101C verifies the details of the acquired progress information (Step S302).

When each of the radiation imaging apparatus 101B and 101C confirms the examination cancel, each of the radiation imaging apparatus 101B and 101C changes the status of the examination concerned to "examination is available to start" as from FIG. 4B to FIG. 4A (Step S305), and stores the change. In this case, the radiation imaging apparatus 101A may also change the status of the examination concerned to "examination is available to start" as from FIG. 4B to FIG. 4A and store the change.

As described above, when the imaging apparatus control unit 109 of each of the radiation imaging apparatus 101B and 101C acquires the first progress information representing that the imaging of the first radiation image is canceled, the imaging apparatus control unit 109 of each of the radiation imaging apparatus 101B and 101C permits the imaging of the second radiation image. When the imaging apparatus control unit 109 of each of the radiation imaging apparatus 101B and 101C acquires the first progress information representing that the imaging of the first radiation image is canceled, the imaging apparatus control unit 109 of each of the radiation imaging apparatus 101B and 101C updates the second progress information to progress information representing that the imaging of the second radiation image is available to start.

In order to prevent the plurality of radiation imaging apparatus 101 from informing each other of the progress information of the same examination at the same time, the radiation imaging apparatus 101A rejects the progress information informed from the other radiation imaging apparatus 101B and 101C from the start of the informing of the progress information to the completion of the informing of the progress information. Further, when there is a radiation imaging apparatus 101 that rejects the informed progress information, after waiting for a predetermined time period, the radiation imaging apparatus 101A informs the radiation imaging apparatus 101 that has rejected the informed progress information of the progress information of the examination concerned again.

According to the first embodiment, even when the plurality of radiation imaging apparatus store the duplicating examination information, the examination can be prevented from being performed in a duplicated manner.

Second Embodiment

An operation of a radiation imaging system according to a second embodiment of the present invention is described. The radiation imaging system according to the second embodiment avoids performing the same examination in a duplicated manner along the flow of the examination. The radiation imaging apparatus 101A controls the imaging of the first radiation image based on the second progress information. Description of like configurations, functions, and operations as those in the above-mentioned embodiment is omitted herein, and the difference from the first embodiment is mainly described.

In the second embodiment, similarly to the first embodiment, the radiation imaging apparatus 101 acquires the examination information from the RIS 103 to store the examination information in the storage, but the status stored in association with each examination is at least one of "examination unperformed", "examination start", or "examination end". The status in the initial setting of each examination is "examination is unperformed".

Figure 7:
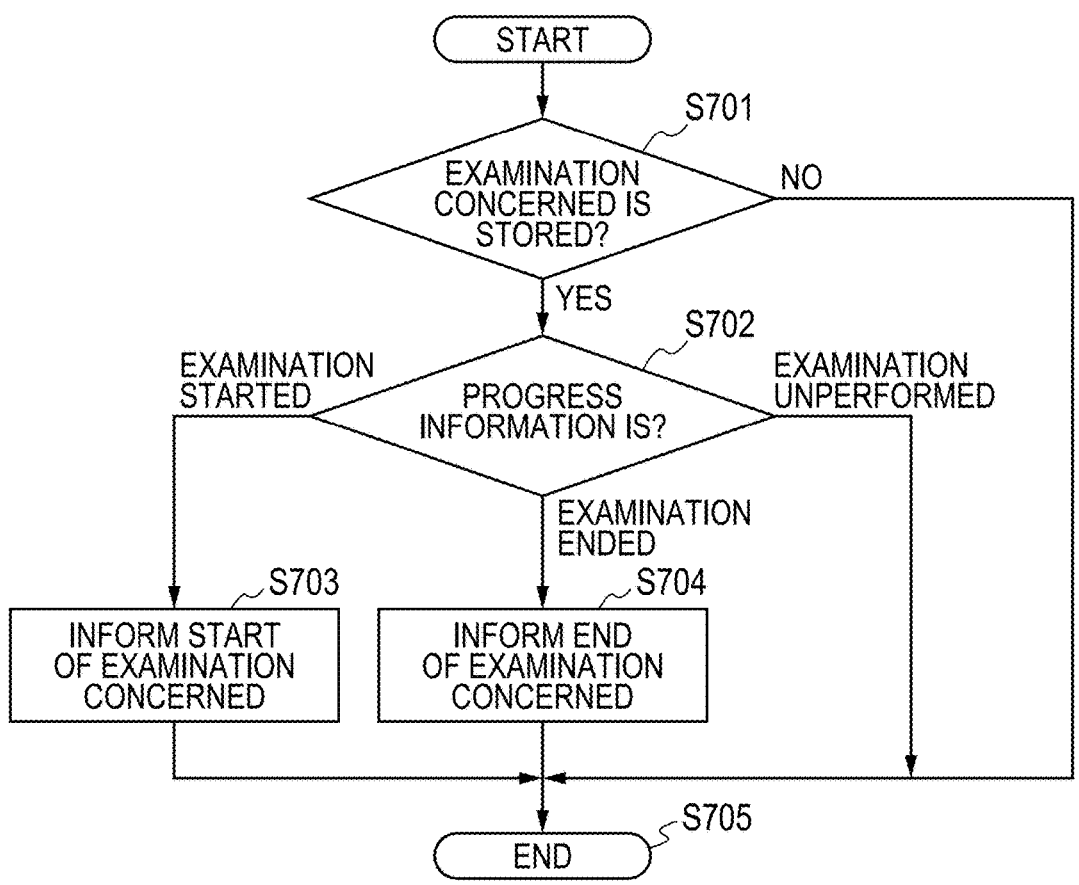
FIG. 7 is a flow chart for illustrating an example of processing performed by a radiation imaging apparatus in a second embodiment of the present invention.

FIG. 7 is a flow chart for illustrating an example of the processing performed by the radiation imaging apparatus 101 in the second embodiment. The radiation imaging apparatus 101A acquires the first examination information from the RIS 103 and stores the first examination information. As illustrated in FIG. 2, the radiation imaging apparatus 101A displays the stored examination information on the examination information list screen. When the operator selects the examination information from the examination information selection section 202, the radiation imaging apparatus 101A requests the radiation imaging apparatus 101B and 101C to acquire the progress information of the examination concerned.

Each of the radiation imaging apparatus 101B and 101C that has received the request of acquiring the examination progress information determines whether or not the examination information is stored (Step S701). When the examination information is not stored, each of the radiation imaging apparatus 101B and 101C ends the communication without transmitting the progress information (Step S705). When the examination information is stored, each of the radiation imaging apparatus 101B and 101C verifies the status stored in association with the examination concerned (Step S702). The imaging apparatus control unit 109 of each of the radiation imaging apparatus 101B and 101C transmits the second progress information to the radiation imaging apparatus 101A when predetermined examination information is duplicated between the first examination information and the second examination information.

When the status is "examination start", each of the radiation imaging apparatus 101B and 101C transmits information representing "examination start" to the radiation imaging apparatus 101A (Step S703). When the status is "examination end", each of the radiation imaging apparatus 101B and 101C transmits information representing "examination end" to the radiation imaging apparatus 101A (Step S704).

When the imaging apparatus control unit 109 of the radiation imaging apparatus 101A acquires the second progress information representing that the imaging of the second radiation image is started, the imaging apparatus control unit 109 of the radiation imaging apparatus 101A does not permit the imaging of the first radiation image. When the imaging apparatus control unit 109 of the radiation imaging apparatus 101A acquires the second progress information representing that the imaging of the second radiation image is started, the imaging apparatus control unit 109 of the radiation imaging apparatus 101A may update the first progress information to progress information representing that the imaging of the first radiation image is unavailable to start.

Further, when the control unit of the first radiation imaging apparatus acquires the second progress information representing that the imaging of the second radiation image is ended, the control unit of the first radiation imaging apparatus deletes the first examination information from the storage unit of the first radiation imaging apparatus.

When the status is "examination unperformed", each of the radiation imaging apparatus 101B and 101C ends the communication without transmitting the progress information (Step S705).

The determination unit 113 of each of the radiation imaging apparatus 101B and 101C does not transmit the second progress information to the first radiation imaging apparatus when the imaging of the second radiation image is unperformed even if predetermined examination information is duplicated between the first examination information and the second examination information. When the imaging apparatus control unit 109 of the radiation imaging apparatus 101A does not acquire the second progress information within a predetermined time period, the imaging apparatus control unit 109 of the radiation imaging apparatus 101A permits the imaging of the first radiation image.

In Step S703, when the radiation imaging apparatus 101A acquires "examination start" from at least one of the radiation imaging apparatus 101B or 101C, the radiation imaging apparatus 101A displays an alert to inform the operator that the examination has already been started by any one of the radiation imaging apparatus 101B and 101C.

Further, when the radiation imaging apparatus 101A acquires "examination start" from at least one of the radiation imaging apparatus 101B or 101C, the radiation imaging apparatus 101A may avoid starting the examination in a duplicated manner by inhibiting transition from the examination information list screen to the imaging screen. At this time, the radiation imaging apparatus 101A may be informed of the installation place of the radiation imaging apparatus 101 that has started the examination or the name of the operator using the apparatus.

In Step S704, when the radiation imaging apparatus 101A acquires "examination end" from at least one of the radiation imaging apparatus 101B or 101C, the radiation imaging apparatus 101A displays an alert to inform the operator that the examination has already been ended, and deletes the examination information from the storage. The examination deleted from the storage is no longer displayed on the examination information list screen.

In Step S705, when the radiation imaging apparatus 101A ends the communication without acquiring the progress information from the radiation imaging apparatus 101B and 101C, the radiation imaging apparatus 101A changes the status to "examination start" as from FIG. 8A to FIG. 8B, and stores the change. Then, the radiation imaging apparatus 101A informs the RIS 103 of the examination start of the examination. The imaging apparatus control unit 109 of the radiation imaging apparatus 101A transmits the first progress information to the RIS (information management unit) 103. After that, the radiation imaging apparatus 101A displays the imaging screen on the imaging apparatus display unit 107, and starts the examination.

When the imaging of the second radiation image is unperformed, the determination unit 113 of each of the radiation imaging apparatus 101B and 101C may transmit the second progress information representing that the imaging of the second radiation image is unperformed to the radiation imaging apparatus 101A. When the imaging apparatus control unit 109 of the radiation imaging apparatus 101A acquires the second progress information representing that the imaging of the second radiation image is unperformed, the imaging apparatus control unit 109 of the radiation imaging apparatus 101A permits the imaging of the first radiation image.

After the examination by the radiation imaging apparatus 101A is ended, the operator presses the examination end button 507 displayed on the imaging screen. With this, the examination is ended, and the examination information list screen is displayed on the imaging apparatus display unit 107. At this time, the radiation imaging apparatus 101A changes the status of the examination concerned to "examination end" as from FIG. 8B to FIG. 8C, and stores the change. Further, the radiation imaging apparatus 101A informs the RIS 103 of the examination end of the examination concerned. The imaging apparatus control unit 109 of the radiation imaging apparatus 101A transmits the first progress information to the RIS (information management unit) 103.

The taken radiation image is output to the PACS 104, the printer 105, and the storage of the own apparatus.

Next, description is given of a case in which the radiation imaging apparatus 101A cancels the examination due to the physical condition of the subject or for the sake of operation after the examination is started. When the operator presses the cancel button 506, the examination is canceled, and the examination information list screen is displayed on the imaging apparatus display unit 107. At this time, the radiation imaging apparatus 101A informs the RIS 103 of the examination cancel of the examination concerned. After the informing is completed, the radiation imaging apparatus 101A changes the status of the examination concerned to "examination unperformed" as from FIG. 8B to FIG. 8A, and stores the change.

Next, description is given of a case in which the radiation imaging apparatus 101B and 101C cancel the examination due to the physical condition of the subject or for the sake of operation after the examination is started. When the imaging apparatus control unit 109 of the radiation imaging apparatus 101A acquires the second progress information representing that the imaging of the second radiation image is canceled, the imaging apparatus control unit 109 of the radiation imaging apparatus 101A permits the imaging of the first radiation image. When the imaging apparatus control unit 109 of the radiation imaging apparatus 101A acquires the second progress information representing that the imaging of the second radiation image is canceled, the imaging apparatus control unit 109 of the radiation imaging apparatus 101A updates the first progress information to progress information representing that the imaging of the first radiation image is unperformed.

In order to prevent the plurality of radiation imaging apparatus 101 from requesting each other the progress information of the same examination at the same time, the radiation imaging apparatus 101A performs the following operation. When the radiation imaging apparatus 101A receives an acquisition request from another radiation imaging apparatus 101B while requesting acquisition of the second progress information of the examination concerned, the radiation imaging apparatus 101A displays an alert to inform the operator of the information of the radiation imaging apparatus 101A that has requested the progress information at the same time. In this case, the radiation imaging apparatus 101A discards the second progress information acquired due to the acquisition request so far, and returns to the examination information list screen without starting the examination.

According to the second embodiment, even when the plurality of radiation imaging apparatus store the duplicating examination information, the examination can be prevented from being performed in a duplicated manner.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-035851, filed Feb. 28, 2017 which is hereby incorporated by reference herein in its entirety.

What is claimed is:

1. A radiation imaging system, comprising:
    a first radiation imaging apparatus, which is configured to be capable of taking a first radiation image based on first examination information;
    a second radiation imaging apparatus, which is configured to be capable of taking a second radiation image based on second examination information; and
    a control unit, which is configured to control imaging of the second radiation image in the second radiation imaging apparatus based on progress information related to imaging of the first radiation image in the first radiation imaging apparatus when predetermined examination information is duplicated between the first examination information and the second examination information.

2. A radiation imaging system according to claim 1, further comprising a determination unit, which is configured to acquire the first examination information of the first radiation imaging apparatus to determine duplication between the first examination information and the second examination information.

3. A radiation imaging system according to claim 1,
    wherein the second radiation imaging apparatus includes the control unit, and
    wherein, when the control unit of the second radiation imaging apparatus acquires the progress information representing that the imaging of the first radiation image is started, the control unit of the second radiation imaging apparatus inhibits the imaging of the second radiation image.

4. A radiation imaging system according to claim 3,
    wherein, when the control unit of the second radiation imaging apparatus acquires the progress information representing that the imaging of the first radiation image is started, the control unit of the second radiation imaging apparatus updates progress information related to the imaging of the second radiation image to progress information representing that the imaging of the second radiation image is unavailable to start.

5. A radiation imaging system according to claim 1,
    wherein the second radiation imaging apparatus includes:
        the control unit; and
        a storage unit, which is configured to store the second examination information, and
    wherein, when the control unit of the second radiation imaging apparatus acquires the progress information representing that the imaging of the first radiation image is ended, the control unit of the second radiation imaging apparatus deletes the second examination information from the storage unit of the second radiation imaging apparatus.

6. A radiation imaging system according to claim 1,
    wherein the second radiation imaging apparatus includes the control unit, and
    wherein, when the control unit of the second radiation imaging apparatus acquires the progress information representing that the imaging of the first radiation image is canceled, the control unit of the second radiation imaging apparatus permits the imaging of the second radiation image.

7. A radiation imaging system according to claim 6, wherein, when the control unit of the second radiation imaging apparatus acquires the progress information representing that the imaging of the first radiation image is canceled, the control unit of the second radiation imaging apparatus updates progress information related to the imaging of the second radiation image to progress information representing that the imaging of the second radiation image is available to start.

8. A radiation imaging system according to claim 1, wherein the first radiation imaging apparatus includes a control unit, which is configured to acquire the first examination information from an information management unit configured to manage the examination information, and to transmit the progress information related to the imaging of the first radiation image to the information management unit.

9. A radiation imaging system according to claim 1, wherein the first radiation imaging apparatus includes a control unit, which is configured to transmit the progress information related to the imaging of the first radiation image to the second radiation imaging apparatus.

10. A radiation imaging system, comprising:
a first radiation imaging apparatus, which is configured to be capable of taking a first radiation image based on first examination information; and
a second radiation imaging apparatus, which is configured to be capable of taking a second radiation image based on second examination information,
the second radiation imaging apparatus including:
a determination unit, which is configured to acquire the first examination information of the first radiation imaging apparatus to determine duplication between the first examination information and the second examination information; and
a control unit, which is configured to transmit progress information related to imaging of the second radiation image to the first radiation imaging apparatus when predetermined examination information is duplicated between the first examination information and the second examination information,
the first radiation imaging apparatus including a control unit, which is configured to control imaging of the first radiation image based on the progress information related to the imaging of the second radiation image.

11. A radiation imaging system according to claim 10, wherein, when the control unit of the first radiation imaging apparatus acquires the progress information representing that the imaging of the second radiation image is started, the control unit of the first radiation imaging apparatus inhibits the imaging of the first radiation image.

12. A radiation imaging system according to claim 11, wherein, when the control unit of the first radiation imaging apparatus acquires the progress information representing that the imaging of the second radiation image is started, the control unit of the first radiation imaging apparatus updates progress information related to the imaging of the first radiation image to progress information representing that the imaging of the first radiation image is unavailable to start.

13. A radiation imaging system according to claim 10,
wherein the first radiation imaging apparatus further includes a storage unit, which is configured to store the first examination information, and
wherein, when the control unit of the first radiation imaging apparatus acquires the progress information representing that the imaging of the second radiation image is ended, the control unit of the first radiation imaging apparatus deletes the first examination information from the storage unit of the first radiation imaging apparatus.

14. A radiation imaging system according to claim 10, wherein, when the control unit of the first radiation imaging apparatus acquires the progress information representing that the imaging of the second radiation image is unperformed, the control unit of the first radiation imaging apparatus permits the imaging of the first radiation image.

15. A radiation imaging system according to claim 10,
wherein, even if the predetermined examination information is duplicated between the first examination information and the second examination information, in a case where the imaging of the second radiation image is unperformed, the determination unit inhibits transmission of the progress information related to the imaging of the second radiation image to the first radiation imaging apparatus, and
wherein, when the control unit of the first radiation imaging apparatus does not acquire the progress information related to the imaging of the second radiation image within a predetermined time period, the control unit of the first radiation imaging apparatus permits the imaging of the first radiation image.

16. A radiation imaging system according to claim 10, wherein, when the control unit of the first radiation imaging apparatus acquires the progress information representing that the imaging of the second radiation image is canceled, the control unit of the first radiation imaging apparatus permits the imaging of the first radiation image.

17. A radiation imaging system according to claim 16, wherein, when the control unit of the first radiation imaging apparatus acquires the progress information representing that the imaging of the second radiation image is canceled, the control unit of the first radiation imaging apparatus updates the progress information related to the imaging of the first radiation image to progress information representing that the imaging of the first radiation image is unperformed.

18. A radiation imaging apparatus, comprising:
a second radiation imaging apparatus, which is configured to acquire first examination information from a first radiation imaging apparatus configured to be capable of taking a first radiation image based on the first examination information,
the second radiation imaging apparatus being configured to be capable of taking a second radiation image based on second examination information,
the second radiation imaging apparatus including a control unit, which is configured to control imaging of the second radiation image in the second radiation imaging apparatus based on progress information related to imaging of the first radiation image in the first radiation imaging apparatus when predetermined examination information is duplicated between the first examination information and the second examination information.

19. A radiation imaging method, which is to be performed by a first radiation imaging apparatus configured to be capable of taking a first radiation image based on first examination information and a second radiation imaging apparatus configured to be capable of taking a second radiation image based on second examination information,
the method comprising controlling imaging of the second radiation image in the second radiation imaging apparatus based on progress information related to imaging of the first radiation image in the first radiation imaging apparatus when predetermined examination information is duplicated between the first examination information and the second examination information.

20. A non-transitory computer-readable medium having stored thereon a program to be executed by a processor to cause the processor to execute each step of the radiation imaging method of claim 19.

21. A radiation imaging system, comprising:
a plurality of radiation imaging apparatuses, each of which is configured to be capable of taking a radiation image based on a corresponding examination information; and
a control unit configured to control imaging in one of the plurality of radiation imaging apparatuses based on progress information related to imaging in another one of the plurality of radiation imaging apparatuses in a case examination information is common for the one and the another one of the plurality of radiation imaging apparatuses.

22. The radiation imaging system according to claim 21, further comprising a determination unit configured to determine whether examination is common for the one and the another one of the plurality of radiation imaging apparatuses.

23. The radiation imaging system according to claim 21, wherein in a case the control unit acquires the progress information representing that the imaging in the one of the plurality of apparatuses is started, the control unit inhibits the imaging in the another one of the plurality of apparatuses.

24. The radiation imaging system according to claim 21, wherein in a case the control unit acquires the progress information representing that the imaging in the one of the plurality of apparatuses is ended, the control unit cancels the examination information in the another one of the plurality of apparatuses.

25. The radiation imaging system according to claim 21, wherein in a case the control unit acquires the progress information representing that the imaging of one of the plurality of radiation imaging apparatuses is canceled, the control unit permits the imaging in the another one of the plurality of the radiation imaging apparatuses.

* * * * *